United States Patent

Miller

[11] Patent Number: 6,159,959
[45] Date of Patent: Dec. 12, 2000

[54] COMBINED ESTROGEN AND ANTIESTROGEN THERAPY

[75] Inventor: Chris P. Miller, Strafford, Pa.

[73] Assignee: American Home Products Corporation, Madison, N.J.

[21] Appl. No.: 09/306,043

[22] Filed: May 6, 1999

Related U.S. Application Data

[60] Provisional application No. 60/150,685.

[51] Int. Cl.[7] .................. A61K 31/56; A61K 31/445; A61K 31/40
[52] U.S. Cl. ................... 514/171; 514/319; 514/410
[58] Field of Search ................... 514/171, 319, 514/410

[56] References Cited

U.S. PATENT DOCUMENTS

| | | |
|---|---|---|
| 4,656,187 | 4/1987 | Black et al. . |
| 4,894,373 | 1/1990 | Young . |
| 4,943,572 | 7/1990 | von Angerer . |
| 5,023,254 | 6/1991 | von Angerer . |
| 5,051,442 | 9/1991 | Salituro et al. . |
| 5,124,335 | 6/1992 | Patchett et al. . |
| 5,389,641 | 2/1995 | Naka et al. . |
| 5,395,842 | 3/1995 | Labrie et al. . |
| 5,496,844 | 3/1996 | Inai et al. . |
| 5,534,527 | 7/1996 | Black et al. . |
| 5,550,107 | 8/1996 | Labrie . |
| 5,552,401 | 9/1996 | Cullinan et al. . |
| 5,591,753 | 1/1997 | Black et al. . |
| 5,646,137 | 7/1997 | Black et al. . |
| 5,672,609 | 9/1997 | Bryant et al. . |
| 5,852,039 | 12/1998 | Sohda et al. . |

FOREIGN PATENT DOCUMENTS

| | | |
|---|---|---|
| 0166591 | 1/1986 | European Pat. Off. . |
| 0242167 | 10/1987 | European Pat. Off. . |
| 0509762 | 10/1992 | European Pat. Off. . |
| 0510398 | 10/1992 | European Pat. Off. . |
| 94027576 | 5/1996 | Russian Federation . |
| 511841 | 8/1971 | Switzerland . |
| 219596 | 10/1968 | U.S.S.R. . |
| 1123263 | 8/1968 | United Kingdom . |
| 1168450 | 10/1969 | United Kingdom . |
| 1566307 | 4/1980 | United Kingdom . |
| 9113060 | 9/1991 | WIPO . |
| 9310741 | 6/1993 | WIPO . |
| 9323374 | 11/1993 | WIPO . |
| 0639567 | 2/1995 | WIPO . |
| 9517383 | 6/1995 | WIPO . |
| 9522524 | 8/1995 | WIPO . |
| 9603375 | 2/1996 | WIPO . |

OTHER PUBLICATIONS von Angerer et al., J. Med. Chem . . , vol. 33, No. 9, pp. 2635–2640, 1990.
von Angerer et al., J. Med. Chem., vol. 30, No. 1., pp. 132–136, 1987.
Rackeley, Contemporary Treatment in Cardiovascular Disease, 1, pp. 49–58 (1996).
von Angerer et al., Ann. N.Y. Aca. Sci., pp. 176, 177, 189, 1995.
Oparil "Hypertension in postmenopausal Woman:Pathology and Management" EMBASE 95:283951, 1995.
von Angerer et al., J. Med. Chem. vol. 27, pp. 1439–1447, 1984.
Biberger, J. Steroid Biochem. Molec., vol. 58, No. 1, pp. 31–43 (1996).
Bone, vol. 17, No. 4, Oct. 1995, 181S–190S.
Von Angerer, J. Med. Chem. (1983), vol. 26 (1), pp. 113–116.
Kauppila et al., Am. J. Obstet. Gynecol., vol. 140, No. 7, 1981, pp. 787–792.
Kauppila et al., Arch. Gynecol. (1983) 234:49–58.
Segall et al., Eur. J. Med. Chem., 30, No. 2, 165–169 (1995).
Klinicheskaya Farmakologiya i Terapiya, 1996, 5 (1), pp. 70–75.
Klinicheskaya Farmakologiya i Terapiya, 1994, 3 (3), pp. 30–39.

*Primary Examiner*—Raymond Henley, III
*Attorney, Agent, or Firm*—Steven R. Eck

[57] ABSTRACT

The present invention relates to pharmaceutical compositions containing benzo[a]carbazoles or indenoindoles, which are useful as tissue selective estrogenic agents, having the general structures below:

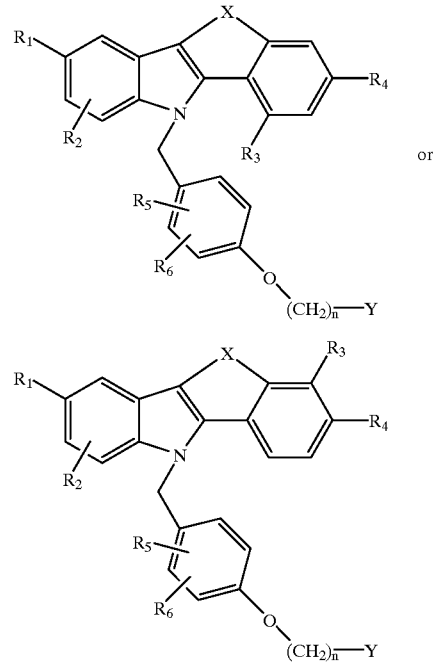

and one or more estrogens and methods of treatment utilizing these formulations.

21 Claims, No Drawings

COMBINED ESTROGEN AND ANTIESTROGEN THERAPY

This application claims the benefit of U.S. Provisional Application No. 60/150,685, which was converted from U.S. patent application Ser. No. 09/076,711, filed May 12, 1998, pursuant to a petition filed under 37 C.F.R. 1.53(c)(2)(i).

The present invention relates to new pharmaceutical compositions containing one or more indenoindole and/or benzocarbazole compounds which are useful as selective estrogen receptor modulating agents and one or more estrogens, as well as methods of treatment utilizing these combined compounds.

BACKGROUND OF THE INVENTION

The use of hormone replacement therapy for bone loss prevention in post-menopausal women is well precedented. The normal protocol calls for estrogen supplementation using such formulations containing estrone, estriol, ethynyl estradiol or conjugated estrogens isolated from natural sources (i.e. Premarin® conjugated estrogens from Wyeth-Ayerst). In some patients, therapy may be contraindicated due to the proliferative effects of unopposed estrogens (estrogens not given in combination with progestins) have on uterine tissue. This proliferation is associated with increased risk for endometriosis and/or endometrial cancer. The effects of unopposed estrogens on breast tissue is less clear, but is of some concern. The need for estrogens which can maintain the bone sparing effect while minimizing the proliferative effects in the uterus and breast is evident. Certain nonsteroidal antiestrogens have been shown to maintain bone mass in the ovariectomized rat model as well as in human clinical trials. Tamoxifen (sold as Novadex® brand tamoxifen citrate by Zeneca Pharmaceuticals, Wilmington, Del.), for example, is a useful palliative for the treatment of breast cancer and has been demonstrated to exert an estrogen agonist-like effect on the bone, in humans. However, it is also a partial agonist in the uterus and this is cause for some concern. Raloxifene, a benzothiophene antiestrogen, has been shown to stimulate uterine growth in the ovariectomized rat to a lesser extent than Tamoxifen while maintaining the ability to spare bone. A suitable review of tissue selective estrogens is seen in the article "Tissue-Selective Actions Of Estrogen Analogs", *Bone* Vol. 17, No. 4, October 1995, 181S–190S.

WO A 95 17383 (Karo Bio AB) describes indole antiestrogens with long straight chains. Another related patent WO A 93 10741 describes 5-Hydroxyindoles with a broad range of side chains. WO 93/23374 (Otsuka Pharmaceuticals, Japan) describes compounds sharing structural similarities with those of the present invention, except with the structure referred to as $R_3$ in the present formulas I and II, below, is defined as thioalkyl and the reference discloses no such compounds having chains from the indole nitrogen having the same structure as the ones provided by the present invention.

In their article *Postmenopausal Hormone replacement therapy with estrogen periodically supplemented with antiestrogen*, Am. J. Obstet. Gynecol., Vol. 140, No. 7, 1981, pp. 787–792, Kauppila et al. describe their study of post-menopausal estrogen therapy of seven-week estrogen regimens followed by 10-day treatments with the antiestrogen clomiphene citrate.

Also, in their article *Comparison of Megestrol Acetate and Clomiphene Citrate as Supplemental Medication in Posmenopausal Oestrogen Replacement Therapy*, Arch. Gynecol. (1983) 234:49–58, Kauppila et al. describe combination therapies in postmenopausal women of estrogen with random supplementation of megestrol acetate or clomiphene citrate.

U.S. Pat. No. 4,894,373 (Young) teaches the use of antiestrogens, including clomiphene and its isomers, citrates and derivatives, in the absence of estrogen for treating menopausal symptoms and treating or preventing osteoporosis. U.S. Pat. No. 5,552,401 (Cullinan et al.) describes benzothiophene compounds as useful for the treatment of various medical indications associated with post-menopausal syndrome, and uterine fibroid disease, endometriosis, and aortal smooth muscle cell proliferation, the compounds being used in pharmaceutical formulations optionally containing estrogen or progestin. U.S. Pat. Nos. 5,646,137 and 5,591,753 (both issued to Black et al.) discloses methods of treating osteoporosis with formulations of raloxefine-type arylbenzothiophene compounds in conjunction with a progestin selected from medroxyprogesterone, norethindrone or norethynodrel, or pharmaceutically acceptable salts thereof. U.S Pat. No. 5,550,107 (Labrie) claims an invention comprising the treatment of breast or endometrial cancer with an antiestrogen together with at least one compound selected from the group of an androgen, a progestin, at least one inhibitor of sex steroid formation, expecially 17β-hydroxysteroid dehydrogenase and aromatase activity, at least one inhibitor of prolactin secretion, one inhibitor of growth hormone secretion and one inhibitor of ACTH secretion. U.S. Pat. No. 5,672,609 (Bryant et al.) discloses pyridine compounds useful in treating post menopausal syndrome and formulations therefore containing estrogen or progestin. U.S. Pat. No. 5,534,527 (Black et al.) teaches the use of aroylbenzothiophenes and estrogens in the inhibition of bone loss.

Indenoindoles and benzocarbazoles, as shown in FIGS. I and II, have not been reported for compounds of the type described bearing the side chain from the nitrogen of the indole as described in the present invention. See Ger. Offen., DE 3821148 Al 891228 and WO 96/03375 describes indenoindoles and benzocarbazoles which do not bear or claim the basic side chains of this invention. Also see Segall, et al, *Eur. J. Med. Chem.*, 30 no #2 165–169 (1995) for benzocarbazoles with estrogenic/antiestrogenic activity.

DESCRIPTION OF THE INVENTION

Indenoindoles and benzo[a]carbazoles of the general structure type shown in FIGS. (I) and (II) are estrogen agonists/antagonists useful for the treatment of diseases associated with estrogen deficiency. The present invention provides pharmaceutical formulations, and methods for using them, comprising compounds of formulas (I) and (II), below, in conjunction with estrogens, preferably in conjunction with one or more pharmaceutically acceptable carriers or excipients. Among the uses of the present formulations is alleviating the symptoms of post-menopausal syndrome in women, including peri-menopausal and post-menopausal symptoms. The present formulations and methods of treatment can be used to minimize undesirable side effects of estrogen treatment or therapy and may be used to minimize the amounts of estrogen(s) necessary for a particular regimen.

Compounds of the general structure type shown in formulas (I) and (II) are estrogen agonists/antagonists useful for the treatment of diseases associated with estrogen deficiency. The compounds of the present invention show strong binding to the estrogen receptor. These compounds have proven to be antiestrogens with little intrinsic estrogenicity. The compounds of formula (I) are capable of antagonizing the effects of 17β-estradiol while showing little uterine stimulation when dosed alone.

The present invention includes compounds of formulas (I) or (II), below:

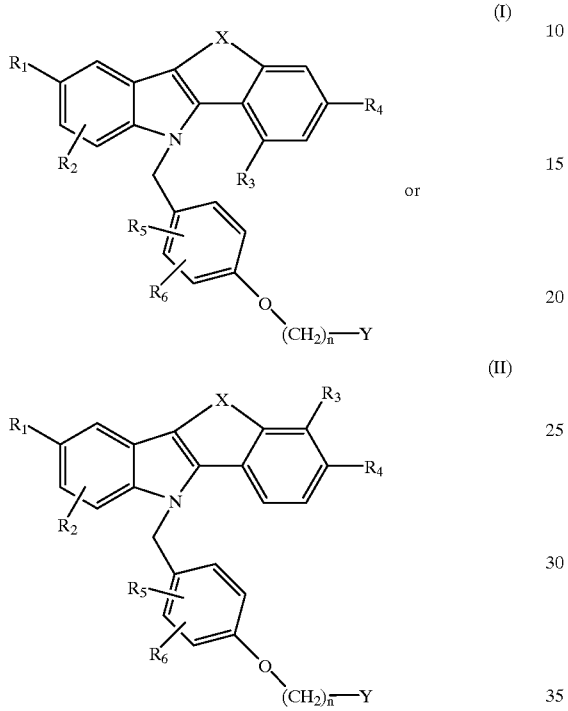

wherein:

$R_1$ is selected from H, OH or the $C_1$–$C_{12}$ esters (straight chain or branched) or C1–C12 (straight chain or branched or cyclic) alkyl ethers thereof, or halogens; or halogenated ethers including trifluoromethyl and trichloromethyl ethers;

$R_2$, $R_3$, $R_4$, $R_5$, and $R_6$ are independently selected from H, OH or the $C_1$–$C_{12}$ esters (straight chain or branched) or C1–C12 alkyl ethers (straight chain or branched or cyclic) thereof, halogens, or halogenated ethers including trifluoromethyl ether and trichloromethyl ether, cyano, $C_1$–$C_6$ alkyl (straight chain or branched), or trifluoromethyl, with the proviso that, when $R_1$ is H, $R_2$ is not OH;

X is —CH═CH— or $(CH_2)_n$.

$n^+$ is 1 or 2 n is 2 through 4;

Y is selected from:
a) the moiety:

wherein $R_7$ and $R_8$ are independently selected from the group of H, $C_1$–$C_6$ alkyl, or phenyl; or
b) a five-membered saturated, unsaturated or partially unsaturated heterocycle containing up to two heteroatoms selected from the group consisting of —O—, —NH—, —N($C_1C_4$ alkyl)—, —N═, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, phenyl optionally substituted with 1–3 ($C_1$–$C_4$)alkly, —CO$_2$H—, —CN—, —CONHR$^1$—, —NH$_2$—, $C_1$–$C_4$ alkylamino, $C_1$–$C_4$ dialkylamino, —NHSO$_2$R$^1$—, —NHCOR$^1$—, —NO$_2$; or c) a six-membered saturated, unsaturated or partially unsaturated heterocycle containing up to two heteroatoms selected from the group consisting of —O—, —NH—, —N($C_1C_4$ alkyl)—, —N═, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, phenyl optionally substituted with 1–3 ($C_1$–$C_4$)alkyl, —CO$_2$H—, —CN—, —CONHR$^1$—, —NH$_2$—, $C_1$–$C_4$ alkylamino, $C_1$–$C_4$ dialkylamiino, —NHSO$_2$R$^1$—, —NHCOR$^1$—, —NO$_2$; or d) a seven-membered saturated, unsaturated or partially unsaturated heterocycle containing up to two heteroatoms selected from the group consisting of —O—, —NH—, —N($C_1C_4$ alkyl)—, —N═, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, phenyl optionally substituted with 1–3 ($C_1$–$C_4$)alkyl, —CO$_2$H—, —CN—, —CONHR$^1$—, —NH$_2$—, $C_1$–$C_4$ dialkylamino, —NHSO$_2$R$^1$—, —NHCOR$^1$—, —NO$_2$—; or e) a bicyclic heterocycle containing from 6–12 carbon atoms either bridged or fused and containing up to two heteroatoms selected from the group consisting of —O—, —NH—, —N($C_1C_4$ alkyl)—, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, phenyl optionally substituted with 1–3 ($C_1$—$C_4$)alkyl, —CO$_2$H—, —CN—, —CONHR$^1$—, —NH$_2$—, $C_1$–$C_4$ alkylamino, $C_1$–$C_4$dialkylamino, —NHSO$_2$R$^1$—, —NHCOR$^1$—, —NO$_2$;

or a pharmaceutically acceptable salt thereof.

The more preferred formulations and methods of treatment of this invention are those having or utilizing, along with one or more pharmaceutical carriers or excipients:

a) one or more estrogens or the mammalian conjugates thereof, such as sulfates or glucoronides; and b) one or more compounds selected from the general structures (I) or (II), above, wherein:

$R_1$ is selected from H, OH or the $C_1$–$C_4$ esters or alkyl ethers thereof, halogen;

$R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;

Y is the moiety

$R_7$ and $R_8$ are selected independently from H, $C_1$–$C_6$ alkyl, or combined by —$(CH_2)p$—, wherein p is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$), —$NH_2$, $C_1$–$C_4$ alkylamino, $C_1$–$C_4$ dialkylamino, —$NHSO_2$($C_1$–$C_4$), —NHCO ($C_1$–$C_4$), and —$NO_2$;

and the pharmaceutically acceptable salts thereof.

The rings formed by a concatenated $R_7$ and $R_8$, mentioned above, may include, but are not limited to, aziridine, azetidine, pyrrolidine, piperidine, hexamethyleneinine or heptamethyleneimine rings.

The most preferred compositions and method of treatment of the present invention are those utilizing compounds the structural formulas (I) or (II), above, wherein $R_1$ is OH; $R_2$–$R_6$ are as defined above; and Y is the moiety

and $R_7$ and $R_8$ are concatenated together as —$(CH_2)_r$—, wherein r is an integer of from 4 to 6, to form a ring optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$), —$NH_2$, $C_1$–$C_4$ alkylamino, $C_1$–$C_4$ dialkylamino, —$NHSO_2$ ($C_1$–$C_4$), —NHCO($C_1$–$C_4$), and —$NO_2$;

and the pharmaceutically acceptable salts thereof.

The invention includes acceptable salt forms of the compounds of Formulas (I) or (II) formed from the addition reaction with either inorganic or organic acids. Inorganic acids such as hydrochloric acid, hydrobromic acid, hydroiodic acid, sulfuric acid, phosphoric acid, nitric acid are useful as well as organic acids such as acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, benzenesulfonic acid. It is known that compounds possessing a basic nitrogen can be complexed with many different acids (both protic and not protic) and usually it is preferred to administer a compound of this invention in the form of an acid addition salt. Additionally, this invention includes quaternary ammonium salts of the compounds herein, which can be prepared by reacting the nucleophilic amines of the side chain with a suitably reactive alkylating agent such as an alkyl halide or berizyl halide.

The compounds of Formulas (I) and (II) are partial estrogen agonists and display high affinity for the estrogen receptor. Unlike many estrogens, however, these compounds do not cause increases in uterine wet weight. These compounds are antiestrogenic in the uterus and can completely antagonize the trophic effects of estrogen agonists in uterine tissue. These compounds are useful in treating or preventing mammal disease states or syndromes which are caused or associated with an estrogen deficiency. This tissue selectivity allows their use for desirable estrogenic activity in certain tissues, such as bone, while limiting that activity in others, such as uterine tissue.

Estrogens useful in the formulations of this invention include estrone, equilin, equilenin, ethinyl estradiol, 17β-estradiol, dihydroequilenin, 17β-dihydroequilenin (U.S. Pat. No. 2,834,712), menstranol and conjugated estrogenic hormones, such as those in Wyeth-Ayerst Laboratories' Premarin® products, as well as the sulfated esters of these estrogens. Also useful in the present formulations are Sodium estrone sulfate, Sodium equilin sulfate, Sodium 17alpha-dihydroequilin sulfate, Sodium 17alpha-estradiol sulfate, Sodium Delta8,9-dehydroestrone sulfate, Sodium equilenin sulfate, Sodium 17beta-dihydroequilin sulfate, Sodium 17alpha-dihydroequilenin sulfate, Sodium 17beta-estradiol sulfate, Sodium 17beta-dihydroequilenin sulfate, Estrone 3-sodium sulfate, Equilin 3-sodium sulfate, 17alpha-Dihydroequilin 3-sodium sulfate, 3beta-Hydroxy-estra-5(10),7-dien-17-one 3-sodium sulfate, 5alpha-Pregnan-3beta-20R-diol 20-sodium sulfate, 5alpha-Pregnan-3beta,16alpha-diol,20-one 3-sodium sulfate, delta (8,9)-Dehydroestrone 3-sodium sulfate, Estra-3beta, 17alpha-diol 3-sodium sulfate, 3beta-Hydroxy-estr-5(10)-en,17-one 3-sodium sulfate or 5alpha-Pregnan-3beta, 16alpha,20R-triol 3-sodium sulfate. Esterified estrogens, such as those sold by Solvay Pharmaceuticals, Inc. under the Estratab® tradename, may also be used with the present formulations. Preferred salts of estrone include, but are not limited to, the sodium and piperate salts. Phytoestrogens, such as equol or enterolactone, may also be used in the present formulations and methods. Mammalian metabolic conjugates of estrogens hereunder, such as the sulfates or glucoronides thereof, may be preferred. A particularly preferred embodiment of this invention comprises pharmaceutical compositions and methods of treatment utilizing conjugated estrogenic hormones, such as those in Wyeth-Ayerst Laboratories' Premarin® products, with one or more compounds of Formulas (I) or (III) listed herein.

The present compounds of Formulas (I) and (II) are tissue selective compounds having the ability to behave like estrogen agonists, such as by lowering cholesterol and preventing bone loss, or like estrogen antagonists. Therefore, these compounds in the present formulations are useful for treating many maladies including osteoporosis, prostatic hypertrophy, infertility, breast cancer, endometrial hyperplasia, endometrial cancer, endometriosis, cystic glandular hyperplasia, uterine hyperplasia, cervical hyperplasia, benign prostatic hyperplasia, cardiovascular disease, contraception, Alzheimer's disease and melanoma. The formulations of this invention may also be used to treat bone loss resulting from secondary osteoporosis, including that categorized as endocrine in nature, including that resulting from glucocorticoid excess, hyperparathyroidism, hyperthyroidism, hypogonadism, hyperprolactinemia, and diabetes mellitus. The bone loss may also be the drug-induced, such as that resulting from heparin treatments, alcohol consumption, or the use of tobacco, barbiturates or corticosteroids. The drug-induced loss of bone may also stem from treatment with gonadotropin releasing hormone (GnRH or LHRH) or synthetic GnRH antagonists or agonists, such as the leuprolide acetate injectable sold by TAP Pharmaceuticals Inc. under the tradename LUPRON® or the goserelin acetate implant sold by Zeneca Pharmaceuticals under the Zoladex® tradename. Such bone loss may also result from immobilization of the individual, chronic renal failure, malabsorption syndrome, hepatic disease, chronic obstructive lung disease, rheumatoid arthritis, or sarcoidosis.

Additionally, these formulations can be used for hormone replacement therapy in post-menopausal women or in other estrogen deficiency states where estrogen supplementation would be beneficial. The symbiotic activity of the compounds, and estrogen(s) of the present methods of treatment are particularly of interest in overcoming the unwanted consequences of estrogen therapy, such as breakthrough bleeding and/or excessive endometrial stimulation, which may lead to endometrial hyperplasia. These formulations, therefore, may be used in methods of treating or preventing excessive estrogenic uterine stimulation in a mammal.

Estrogens regulate a number of physiological processes. The primary target tissues for estrogens include the reproductive tract (ovary; uterus), mammary tissue, skeleton, cardiovascular system and the central nervous system (CNS). The reduction in circulating estrogens results in a number of changes. There is a cessation in reproductive function with an associated amenorrhea, uterine atrophy, and increase in vaginal dryness (lack of keratinization). Mammary tissue becomes relatively quiescent. There is an increase in the rate of loss of bone mass (2–7%) compared to the normal 0.5–1.0%/year that is seen in all individuals over the age of 35. A change in lipid profile occurs with increases in Low Density Lipoprotein (LDL) and decreases in High Density Lipoprotein (HDL) commonly measured and an associated increased risk of a cardiovascular event (heart attack, stroke). Changes in the central nervous system include an increase in vasomotor symptoms (hot flush) and potentially changes in cognition and memory.

Estrogen replacement therapy (ERT) normalizes some of these changes, particularly those associated with the cardiovascular system (reduced LDL, increased HDL, reduced risk of heart attack and stroke), the skeleton (maintenance of bone mass, reduced fracture risk), and central nervous system (reduction in frequency and severity of the hot flush). While the reproductive tract responds, it is not all positive. On the positive side, vaginal dryness is alleviated. However, negative uterine responses include hypertrophy and hyperplasia, along with some menstrual-like bleeding. The breast is also affected and there are data correlating exogenous estrogen therapy with an increased risk of breast cancer.

Currently, women with intact uteri are not prescribed estrogens alone, but estrogens in combination with a progestin to reduce uterine stimulation. While the risks of endometrial cancer are reduced to non-hormone treated levels, the other side effects of progestins reduce compliance in women on hormone replacement.

The tissue selective estrogen (TSE) compounds of this invention provide positive skeletal and cardiovascular affects similar to estrogens, without the negative effects associated with the uterus and breast. The combinations of TSEs and estrogens derive the positive effects of estrogens on the CNS, bone and cardiovascular, with the combination providing complimentary or additive effects on the bone and cardiovascular systems. The major variable is the TSEs ability to block estrogenic influence on the uterus and breast, which are the two major negative effects of unopposed estrogens.

The formulations of this invention may also be used in methods of treatment for bone loss, which may result from an imbalance in an individual's formation of new bone tissues and the resorption of older tissues, leading to a net loss of bone. Such bone depletion results in a range of individuals, particularly in post-menopausal women, women who have undergone hysterectomy, those receiving or who have received extended corticosteroid therapies, those experiencing gonadal dysgenesis, and those suffering from Cushing's syndrome. Special needs for bone replacement can also be addressed using these formulations in individuals with bone fractures, defective bone structures, and those receiving bone-related surgeries and/or the implantation of prosthesis. In addition to those problems described above, these formulations can be used in treatments for osteoarthritis, Paget's disease, osteomalacia, osteohalisteiesis, endometrial cancer, multiple myeloma and other forms of cancer having deleterious effects on bone tissues. Methods of treating the maladies listed herein are understood to comprise administering to an individual in need of such treatment a pharmaceutically effective amount of one or more of the compounds of Formulas (I) and (II), or a pharmaceutically acceptable salt thereof, in conjunction with a therapeutically desirable amount of an estrogen. This invention also includes pharmaceutical compositions utilizing one or more of the present compounds, and/or the pharmaceutically acceptable salts thereof, along with one or more pharmaceutically acceptable carriers, excipients, etc.

It is understood that the dosage, regimen and mode of administration of these compounds of Formulas (I) and (II) will vary according to the malady and the individual being treated and will be subjected to the judgment of the medical practitioner involved. It is preferred that the administration of one or more of the compounds herein begins at a low dose and be increased until the desired effects are achieved. Similarly, it will be understood that the dosage(s) of the estrogen(s) utilized in the present formulations will be selected according to conventional methods. It is most preferred that the dosage will be monitored to achieve the desired result with the minimum of estrogen(s) necessary.

Effective administration of these compounds of Formulas (I) and (II) may be given at a dose of from about 0.01 mg/day to about 1,000 mg/day. Preferably, administration will be from about 1 mg/day to about 600 mg/day in a single dose or in two or more divided doses. Most preferably a daily dose of between about 1 mg/day and about 150 mg/day will be administered. Such doses may be administered in any manner useful in directing the active compounds herein to the recipient's bloodstream, including orally, parenterally (including intravenous, intraperitoneal and subcutaneous injections), and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing one or more estrogens and one or more of the active compounds of Formulas (I) and (II) may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It will be understood that the estrogen of this invention will be administered in the dosages of conventional regimens, according to the recipient's tolerance and the particular treatment or maintenance schedule intended. The compounds of Formulas (I) and (II) herein will be administered in an amount necessary to agonize or antagonize the estrogen(s) of the formulation's activity to the level desired. When conjugated estrogens, USP, are used, it is preferred that the daily doseage is from 0.3 mg to 5.0 mg, more preferably between about 0.3 mg and about 2.5 mg, most preferably between about 0.3 and about 1.25 mg/day. For mestranol a daily dosage may be from about 1 $\mu$g to about 0.15 mg/day and a dosage of from about 1 $\mu$g to about 0.03 mg/day may be used for ethynyl estradiol, preferably between about 5 $\mu$g to about 0.15 mg/day of ethynyl estradiol.

The estrogen(s) and compound(s) of these formulations can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdenmal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached; precise dosages for oral, parenteral, transdermal, rectal or vaginal suppositories, nasal, or intrabronchial and other administrations will be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The compound(s) of Formulas (I) and (II) and the estrogen(s) of the present formulations may be administered in separate dosage units, such as separate pills, tablets, powders, etc., or combined into one formulation. When optimum dosages for the compounds of Formulas (I) and (II) and the estrogens of these formulations have been determined, it may preferable to incorporate both into a single formulation for ease of administration. It is also understood that the formulations herein may or may not include other pharmaceutically active components.

Methods

The synthesis of the compounds described in this invention is accomplished by simply heating either an indanone or a tetralone with the appropriately substituted phenylhydrazine and a protic acid to yield the desired hydrazone which is then cyclized upon further heating with a Lewis acid (e.g. $ZnCl_2$). The indenoindole or benzo[a]carbazole can then be alkylated by deprotonation with a suitably strong base (e.g. NaH) and then treated with the desired side chain. The general scheme for the synthesis of these compounds is illustrated in scheme 1. This concept is illustrated in scheme 2 specifically for the synthesis of compound 6. The synthesis of the side chain 11 is shown in scheme 3.

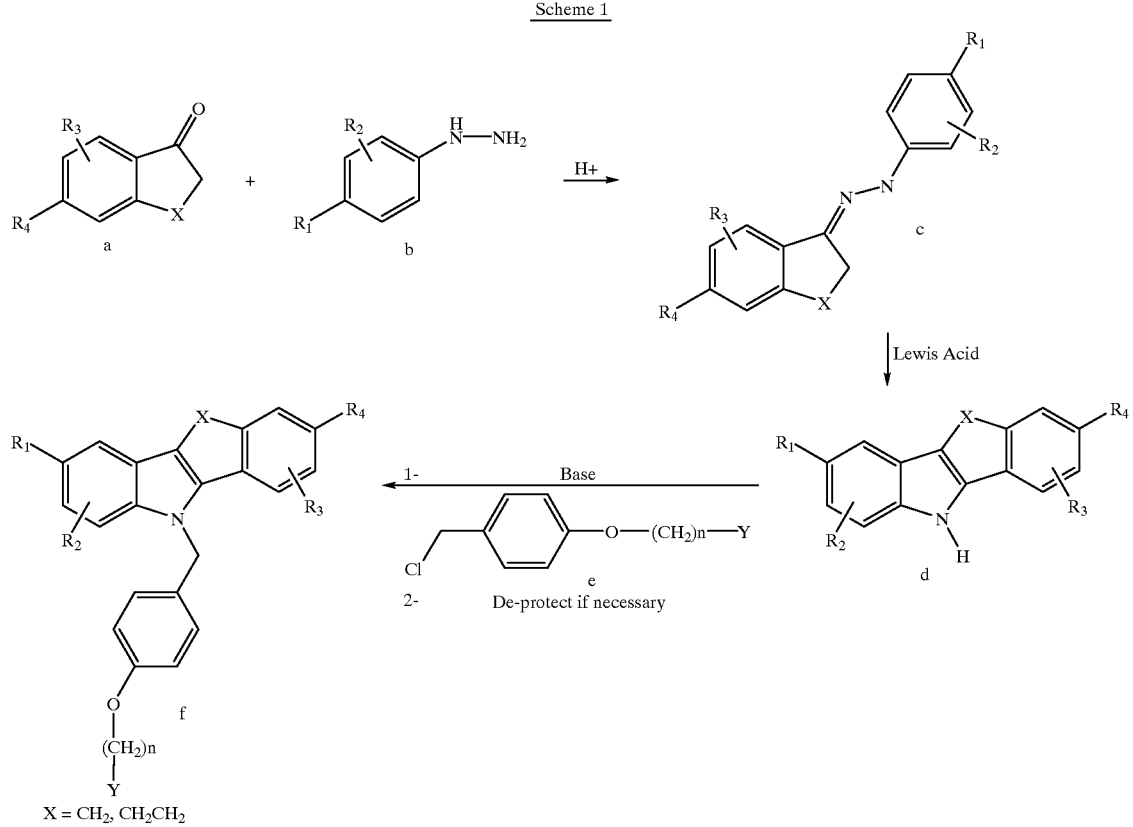

Scheme 1

X = $CH_2$, $CH_2CH_2$

R1, R2, R3, R4, Y, n are as described in Figs 1 and 2

Scheme 2
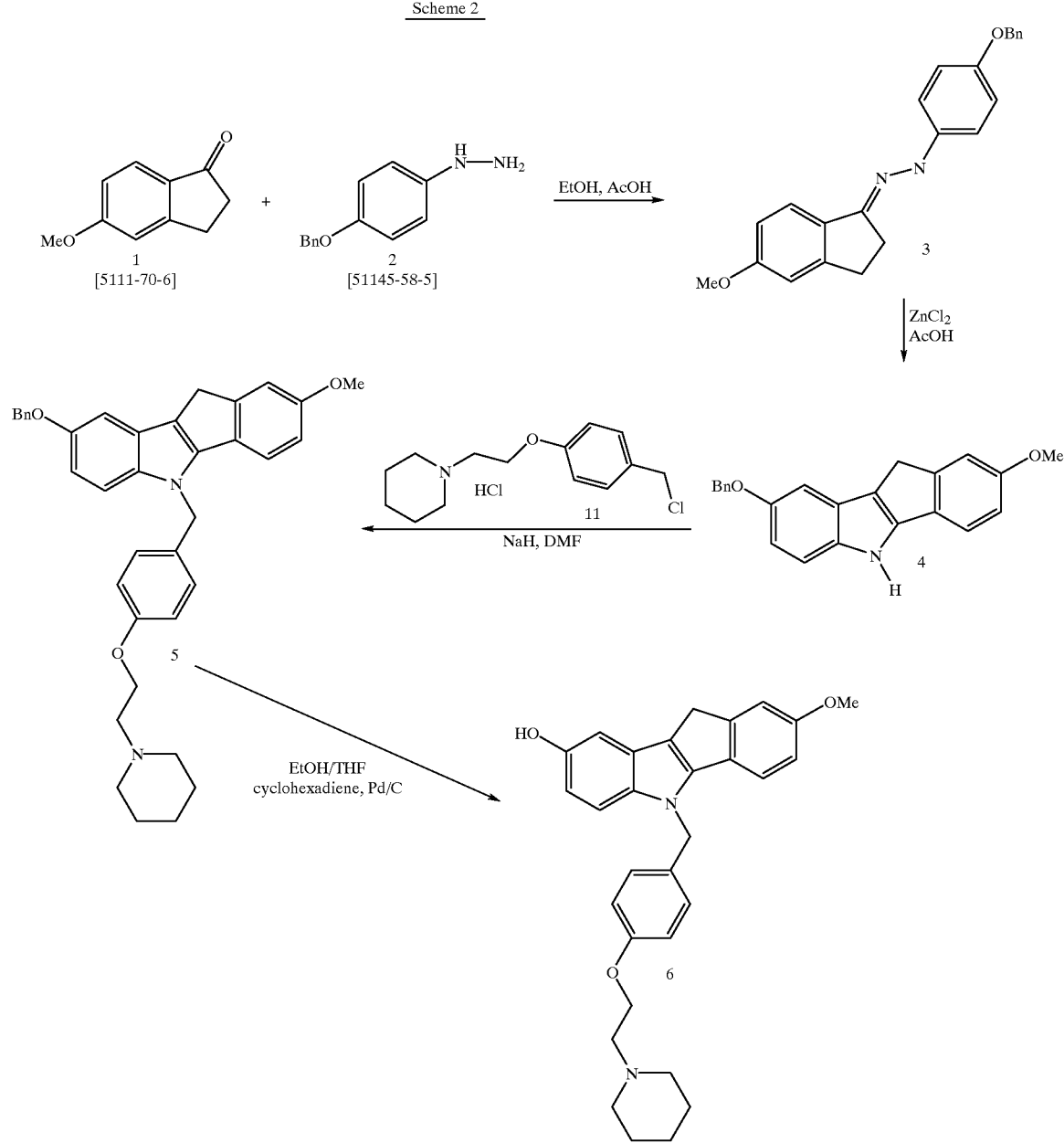

Scheme 3

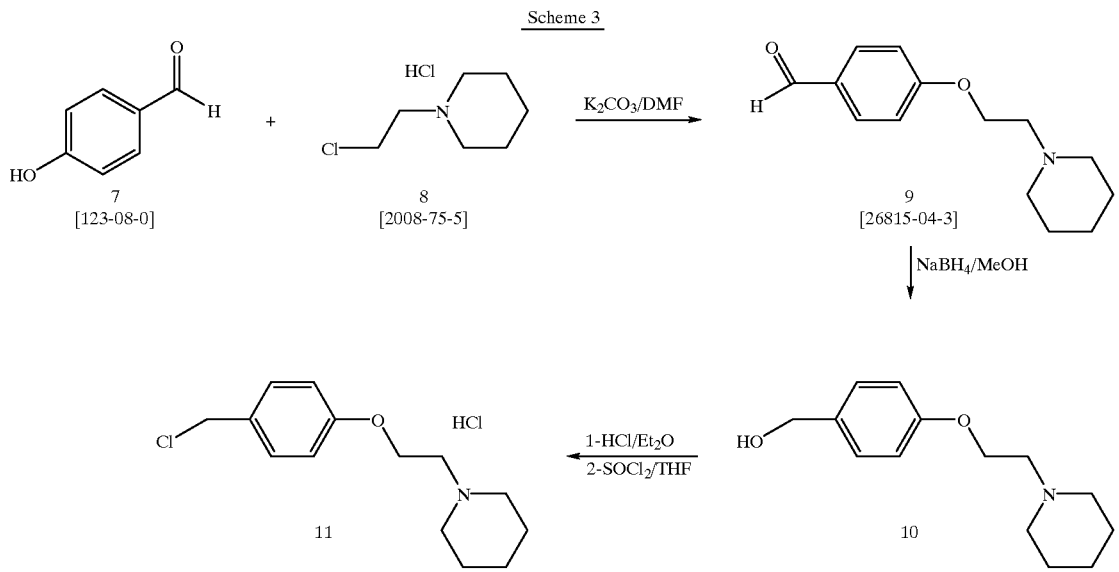

The syntheses of benzo[a]carbazoles (19 through 22) are shown in scheme 4. The tetralone hydrazone 14 is formed from the condensation reaction between 6-methoxy1-tetralone 12 ([1078-19-9] Aldrich Chemical Company) and 4-benzyloxyphenylhydrazine 13 [51145-58-5] in the presence of ethanol and catalytic acetic acid. The hydrazone is then cyclized in the presence of zinc chloride in acetic acid to give the N-unsubstituted benzo[a]carbazole 15. The benzo[a]carbazole can then be alkylated in the same fashion as shown in scheme 1 or 2, or alternatively, as shown in scheme 4, with 4-(2-chloroethoxy)-benzylbromide 17 as the alkylating agent. The chloride is displaced with piperidine or hexamethyleneimine for the examples given, using DMF as the solvent and potassium iodide to facilitate the reaction. The substituted compounds, 19 and 20, are then hydrogenated with cyclohexadiene and a palladium/carbon catalyst to yield compounds 21 and 22.

Scheme 4

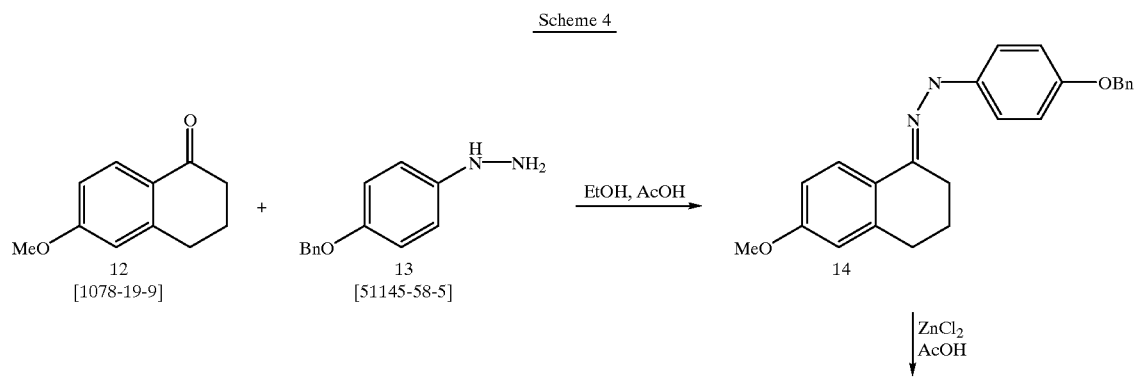

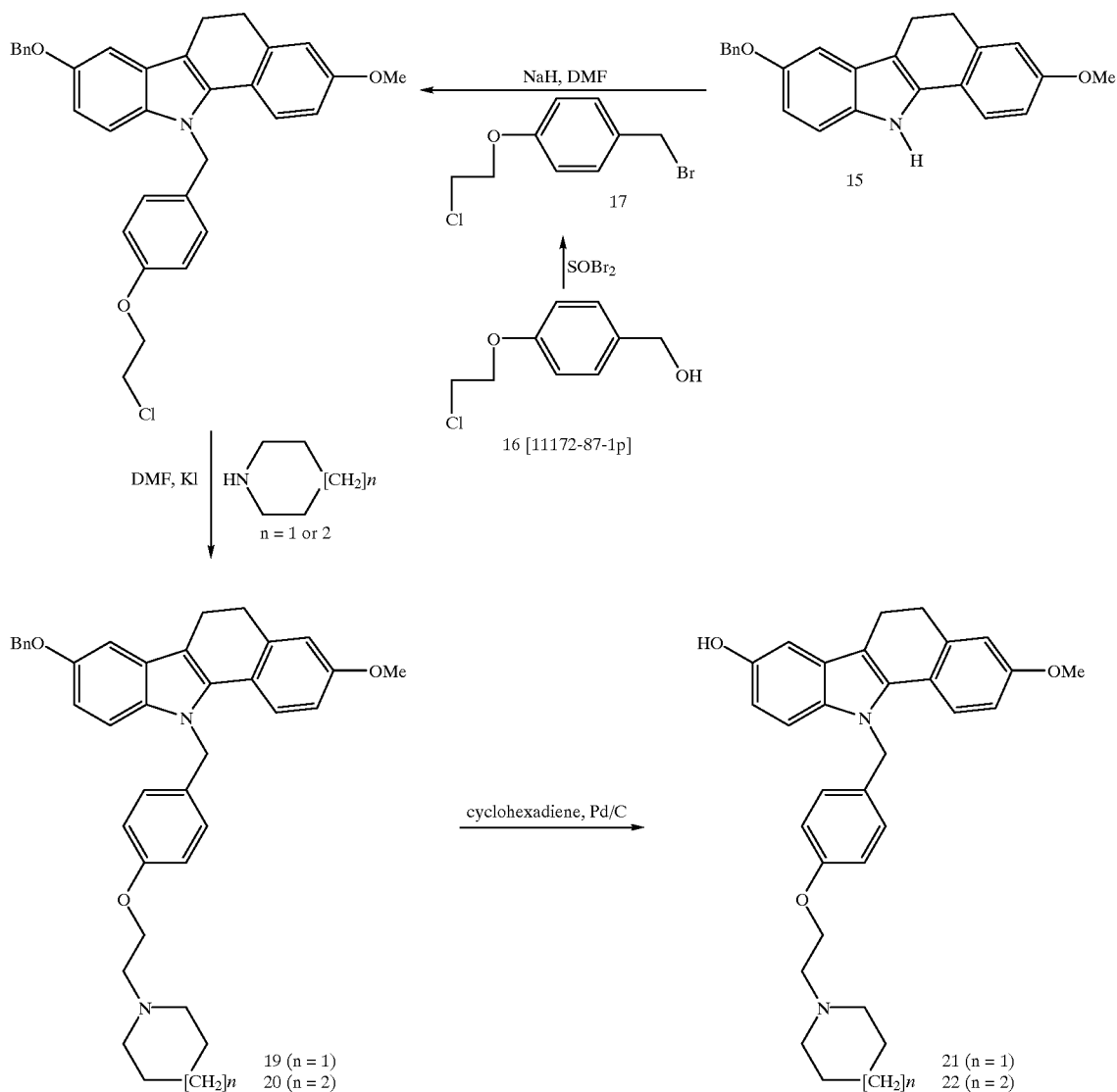

Experimental

Aldrich Sure Seal™ Solvents, anhydrous without further purification, may be used for the reactions described herein and may be obtained from Aldrich Chemical Company. All reactions were carried out under a nitrogen atmosphere. Chromatography was performed using 230–400 mesh silica gel (Merck Grade 60, Aldrich Chemical Company). Thin layer chromatography was performed with Silica Gel 60 $F_{254}$ plates from EM Science. $^1$H NMR spectra were obtained on a Bruker AM-400 instrument in DMSO and chemical shifts reported in ppm. Melting points were determined on a Thomas-Hoover apparatus and are uncorrected. IR spectra were recorded on a Perkin-Elmer diffraction grating or Perkin-Elmer 784 spectrophotometers. Mass spectra were recorded on a Kratos MS 50 or Finnigan 8230 mass spectrometers. Elemental analyses were obtained with a Perkin-Elmer 2400 elemental analyzer. Compounds for which CHN are reported are within 0.4% of the theoretical value for the formula given. Compound nomenclature was typically arrived at by use of the Beilstein Autonom™ program.

Synthesis of indenoindoles and benzocarbazoles

TABLE 1

| Compound # | n | Z | R |
|---|---|---|---|
| Compound 5 (Scheme 2) | 1 | piperidine | Bn |
| Compound 6 (Scheme 2) | 1 | piperidine | H |
| Cmpd. 19 (Scheme 4) | 2 | piperidine | Bn |
| Cmpd. 20 (Scheme 4) | 2 | azepane | Bn |
| Cmpd. 21 (Scheme 4) | 2 | piperidine | H |
| Cmpd. 22 (Scheme 4) | 2 | azepane | H |

EXAMPLE NO. 1

(Intermediate #3 in Scheme 2)

5-Methoxy-1-indanone(4-Benzyloxyphenyl)-hydrazone

A solution of 4-benzyloxyphenylhydrazine [51145-58-5]* (10.0 g, 51 mmole) and 5-methoxy indanone [5111-70-6]** (9 g, 55 mmole) and a few drops of AcOH in EtOH (100 ml) was heated to reflux for 1 hr. The reaction was then cooled and a solid precipitated out. The solid was filtered to give 14 g of a tan solid (80%). $^1$H NMR (DMSO) 11.88 (s, 1H), 7.48 (d, 1H, J=8.4 Hz), 7.43–7.32 (m, 5H), 7.08 (d, 2H, J=9.0 Hz), 6.88 (m, 3H), 6.81 (dd, 1H, J=8.8 Hz, 2.4 Hz), 5.17 (s, 2H), 3.75 (s, 3H), 3.03 (t, 2H, J=6.6 Hz), 2.73 (t, 2H, J=6.5 Hz); IR (KBr) 3350, 1520, 1250 cm$^1$; CHN calc for $C_{23}H_{22}N_2O_2$.

*Prepared by the method given in Miyadera T. and Kosower E. M.:*J.Med.Chem* 15 (1972) 339–340 using 4-benzyloxyaniline (Aldrich Chemical) as the starting material
**Purchased from Aldrich Chemical Company

EXAMPLE NO. 2

(Intermediate #4 in Scheme 2)

2-Methoxy-8-benzyloxy-5,10-dihydro-indeno[1,2-b]indole

A solution of 5-Methoxy-1-indanone(4-Benzyloxyphenyl)-hydrazone (#3 from previous step) (14 g, 41 mmole) and $ZnCl_2$ (14 g, 100 mmol) in AcOH (70 ml) was heated to 110° C. for 30 min. The reaction was then poured into water, extracted with EtOAc. The organic layer was dried with $MgSO_4$ and concentrated. The product was purified by flash chromatography (eluent 20% EtOAc/Hexane) to give a yellow solid. The solid was stirred in ether and filtered to give 2.3 g of an off white solid (17%). Mp=189–193° C.; $^1$H NMR (DMSO) 11.28 (s, 1H), 7.41 (m, 5H), 7.32 (m, 2H), 7.17 (d, 1H, J=2.4 Hz), 7.10 (d, 1H, J=2.4 Hz), 6.89 (dd, 1H, J=8.4 Hz, 2.4 Hz), 6.75 (dd, 1H, J=8.6 Hz, 2.4 Hz), 5.10 (s, 2H), 3.78 (s, 3H), 3.60 (s, 2H); MS eI m/z 342 (M+).

EXAMPLE NO. 3

(Intermediate No. 5 in Scheme 2)

8-Benzyloxy-2-methoxy-5-[4-(2-piperidin-1-yl-ethoxy)-benzyl]-5,10-dihydro-indeno[1,2-b]indole Compound #11 (see procedure below) (5.0 g, 23.9 mmol) in DMF (40 mL) was cooled to 0° C. and treated with NaH (60% dispersion in mineral oil, 1.15 g, 28.8 mmol) and stirred for 15 minutes. The resulting solution was treated with the indenoindole #4 (4.0 g, 11.7 mmol) followed by an additional equivalent of NaH (60% dispersion in mineral oil, 0.47 g, 11.7 mmol). The reaction was allowed to come to room temperature (rt) and stirred for 2 hours. The reaction mixture was poured into water and extracted with ethyl acetate, dried over magnesium sulfate and concentrated. The concentrate was chromatographed on silica gel (ethyl acetate/hexanes, 7:3) then with 100% ethyl acetate which yielded a brown solid which was triturated with methanol to yield 3.2 g of an off-white solid: Mp=102–105° C.; $^1$H NMR (DMSO) 7.52 (d, 1H, J=8.4 Hz), 7.43 (m, 5H), 7.36 (m, 1H), 7.18 (d, 1H, J=2.2 Hz), 7.13 (d, 1H, J=2.4 Hz), 7.04 (d, 2H, J=8.6 Hz), 6.85 (dd, 1H, J=8.3 Hz, 2.4 Hz), 6.80 (m, 3H), 5.58 (s, 2H), 5.10 (s, 2H), 3.93 (t, 2H, J=5.9 Hz), 3.77 (s, 3H), 3.64 (s, 2H), 2.55 (t, 2H, J=5.9 Hz), 2.34 (m, 4H), 1.42 (m, 4H), 1.33 (m, 2H); IR (KBr) 2950, 1460, 1250 cm$^{-1}$; MS eI m/z 559 (M+).

EXAMPLE NO. 4

(Product No. 6 in Scheme 2)

2-Methoxy-5-[4-(2-piperidin-1-yl-ethoxy)-benzyl]-5,10-dihydro-indeno[1,2-b]indol-8ol A solution consisting of 8-Benzyloxy-2-methoxy-5-[4-(2-piperidin-1-yl-ethoxy)-benzyl]-5,10-dihydro-indeno[1,2-b]indole (Example No. 3), 1.6 g 10% Pd/C, and cyclohexadiene (8 mL) and THF/EtOH (approximately 1:1) was stirred at room temperature for 18 hours (h) after which time the reaction mixture was filtered through celite, concentrated and triturated with methanol to yield 2.2 g of a white solid: Mp=144–146° C.; $^1$H NMR (DMSO) 8.74 (s, 1H), 7.48 (d, 1H, J=8.4 Hz), 7.29 (d, 1H, J=8.8 Hz), 7.16 (d, 1H, J=2.2 Hz), 7.04 (d, 2H, J=8.8 Hz), 6.82 (m, 4H), 6.55 (dd, 1H, J=8.8 Hz, 2.2 Hz), 5.53 (s, 2H), 3.93 (t, 2H, J=6.0 Hz), 3.76 (s, 3H), 3.60 (s, 2H), 2.55 (t, 2H, J=5.9 Hz), 2.34 (m, 4H), 1.43 (m, 4H), 1.33 (m, 2H); IR (KBr) 3400, 2910, 1460, 1250 cm$^{-1}$; MS eI m/z 469 (M+); CHN calc for $C_{30}H_{32}N_2O_3$+0.5$H_2O$+0.4 ethanol.

EXAMPLE NO. 5

(Intermediate No. 9 in Scheme 3)

4-(2-piperidin-ethoxy)-benzyl aldehyde

To a well-stirred slurred of p-hydroxybenzaldehyde [123-08-0] (83.5 g, 0.68 mol) and $K_2CO_3$ (224 g, 1.6 mol) in DMF (1 L), 1-(2-chloroethyl)piperidine [2008-75-5] (120 g, 0.65 mol) was added. The reaction mixture was refluxed for 2 hours with vigorous mechanical stirring. After 2 h, the reaction mixture was filtered through celite, diluted with EtOAc (2L), and washed with water (3×500 mL). The organic layer was concentrated to yield 147 g of aldehyde #9 [138351-15-2] as a yellow oil: $^1$H NMR (CDCl$_3$) 9.87 (s, 1H), 7.81 (d, 2H, J=8.7 Hz), 7.02 (d, 2H, J=8.7 Hz), 4.14 (t, 2H, J=6.1 Hz), 2.98 (t, 2H, J=6.1 Hz), 2.78 (m, 4H), 1.66–1.61 (m, 8H).

EXAMPLE NO. 6

(Intermediate No. 10 in Scheme 3)

4-(2-piperidin-ethoxy)-benzyl alcohol

To a stirred solution of the aldehyde #9 (115 g, 0.49 mol) in MeOH (0.36 L) at 0° C., NaBH$_4$ (9.44 g, 0.25 mol) was added portionwise. The reaction was allowed to stir for 30 minutes and then poured into water and extracted with $CH_2Cl_2$ and then dried over MgSO$_4$. The solution was concentrated to give 91.6 g of an oil which crystallized upon seeding: $^1$H NMR (CDCl$_3$) 7.23 (d, 2H, J=8.5 Hz), 6.80 (d, 2H, J=8.5 Hz), 4.56 (s, 2H), 3.99 (t, 2H, J=6.1 Hz), 2.69 (t, 2H, J=6.1 Hz), 2.47 (m, 4H), 1.60–1.25 (m, 6H); $^{13}$C NMR (DMSO) 158.2, 135.3, 128.7, 114.8, 66.4, 63.4, 58.3, 55.3, 26.4, 24.8.

EXAMPLE NO. 7

(Compound No. 11 in Scheme 3)

(4-Chloromethyl-phenoxy)-ethyl-piperidin hydrochloride

A solution of the alcohol #10 (61.3 g, 0.26 mol) in THF (0.5 L) was cooled to 0° C. and gaseous HCL bubbled through. The bubbling was continued until no more thickening was observed. The ice bath used to cool the reaction was removed and SOCl$_2$ (29 mL, 0.39 mol) added and then the mixture heated at 50° C. until the mixture became clear. The reaction mixture was cooled to −3° C. and stirred for 30 minutes. A white solid precipitated out and was filtered and dried to give 72 g of the chloride #11: $^1$H NMR (DMSO) 11.0 (br s, 1H), 7.39 (d, 2H, J=8.5 Hz), 6.99 (d, 2H, J=8.5 Hz), 4.74 (s, 2H), 4.46 (m, 2H), 3.45 (m, 4H), 2.69 (m, 2H), 1.90–1.20 (m, 6H).

EXAMPLE NO. 8 (a)

(Intermediate No. 14 in Scheme 4)

5-Methoxy-1-tetralone-(4-Benzyloxyphenyl)-hydrazone

A solution of 6-methoxy-1-tetralone [1078-19-9]* (14.8 g, 84 mmol) and 4-benzyloxyphenyl hydrazine [5111-70-6]** (15.0 g, 70 mmol) and a few drops of AcOH in EtOH was heated to reflux for 1 hr. The reaction was then cooled and a solid precipitated out. The solid was filtered to give 21.5 g of #14: Mp=86–91° C.; $^1$H NMR (DMSO) 8.8 (s, 1H), 8.00–6.50 (m, 12H), 5.00 (s, 2H), 3.82 (s, 3H), 2.80–2.65 (m, 4H), 1.90 (t, 2H, J=6.0 Hz).

*Aldrich Chemical Company
**Prepared by the method given in Miyadera T. and Kosower E. M.:*J.Med.Chem* 15 (1972) 339–340 using 4-benzyloxyaniline (Aldrich Chemical) as the starting material

EXAMPLE NO. 8 (b)

(Intermediate No. 15 in scheme 4)

3-Methoxy-8-benzyloxy-5,11-dihydro-6H-benzo[a]carbazole

A flask containing hydrazone #14 (23 g, 61.7 mmol), ZnCl$_2$ (21.0 g, 154.4 mmol), and 100 mL AcOH was heated to 95° C. for 10 minutes. The reaction was allowed to come to room temperature and the product precipitated out of the reaction mixture. The product was washed with ether and filtered yielding 21 g of the product #15 as a tan solid: Mp=182–185° C.; $^1$H NMR (DMSO) 11.19 (s, 1H), 7.59–7.36 (m, 6H), 7.26 (d, 1H, J=8.7 Hz), 7.08 (d, 1H, J=2.3 Hz), 6.94–6.87 (m, 2H), 6.79 (dd, 1H, J=8.7 Hz, 2.4 Hz), 5.14 (s, 2H), 3.81 (s, 3H), 2.99 (t, 2H, J=7.1 Hz), 2.86 (t, 2H, J=6.1 Hz).

EXAMPLE NO. 9

(Intermediate No. 17 in scheme 4)

4-(2-Chloroethoxy)-benzylbromide 4-(2-Chloroethoxy)benzyl alcohol #16 [11172-87-1p] (6.4 g, 34.3 mmol) in dioxane (100 mL) at 0° C. was added slowly thionylbromide (7.13 g, 34.3 mmol). The reaction was done at 0°C. after 5 min. The reaction mixture was diluted with ether (200 mL) and washed with H$_2$O (1×30 mL) then NaHCO$_3$ (2×25 mL), and brine (30 mL). The organic extract was dried over MgSO$_4$ and concentrated. The crude product was purified by silica gel chromatography (EtOAC/hexanes; 1:6) to yield 5.0 g (58%) of the desired product #17 as a white solid: Mp=64–66° C.; $^1$H NMR (DMSO) 7.37 (d, 2H, J=8.8 Hz), 6.93 (d, 2H, J=8.8 Hz), 4.68 (s, 2H), 4.24 (t, 2H, J=5.0 Hz), 3.93 (t, 2H, J=5.3 Hz); MS el m/z 248 (M+).

EXAMPLE NO. 10

(Intermediate No. 18 in scheme 4)

11-[4-(2-Chloroethoxy)-benzyl]-8-benzyloxy-3-methoxy-5,11-dihydro-6H-benzo[a]carbazole Benzo[a]carbazole #15 (10 g, 28.1 mmol) in DMF was cooled to 0° C. and treated with NaH (1.66 g, 41.5 mmol) and stirred for 10 minutes. This solution was then added to a solution of 4-(2-Chloroethoxy)benzylbromide #17 (11.2 g, 45.0 mmol) in DMF and the reaction was stirred at 0° C. for 5 minutes and then allowed to stir at room temperature for 20 minutes. The reaction was worked up by quenching with water and extracting with ethyl acetate. The ethyl acetate was washed with brine and dried over MgSO$_4$. The reaction mixture was concentrated to leave 15 g of the product as a crude oil which was used as is for the next reaction: $^1$H NMR (DMSO) 7.52–6.82 (m, 13H), 6.80 (dd, 1H, J=8.4 Hz, 2.6 Hz), 6.75 (dd, 1H, 8.8 Hz, 2.4 Hz), 5.56 (s, 2H), 5.11 (s, 2H), 4.20 (t, 2H, J=6.0 Hz), 3.90 (t, 2H, J=6.2 Hz), 3.73 (s, 3H), 2.92–2.75 (m, 4H).

EXAMPLE NO. 11

(Compound No. 19 in Scheme 4)

3-Methoxy-8-benzyloxy-11-[4-(2-piperidin-1-yl-ethoxy)-benzyl]-5,11-dihydro-6H-benzo[a]carbazole Intermediate #18 (6 g, 11.5 mmol) in DMF was treated with KI (2.5 g, 15.0 mmol) and piperidine (12 mL) and heated to 65° C. for 18 hours. The reaction was worked up by pouring the crude reaction mixture into water and extracting with ethyl acetate. The ethyl acetate layer was washed with NaHCO$_3$ aq., brine and dried over MgSO$_4$. The resultant was chromatographed on silica gel using CH$_2$Cl$_2$ (100%), CH$_2$Cl$_2$:MeOH (98:2), CH$_2$Cl$_2$:MeOH (96:4) as the eluting solvents. The product (3.2 g) was isolated as an oil: $^1$H NMR (DMSO) 7.52–7.12 (m, 8H), 6.98–6.82 (m, 5H), 6.80 (dd, 1H, J=8.4 Hz, 2.6 Hz), 6.73 (dd, 1H, J=8.8 Hz, 2.4 Hz), 5.56 (s, 2H), 5.11 (s, 2H), 3.98 (t, 2H, J=6.0 Hz), 3.70 (s, 3H), 2.85–2.78 (m, 2H), 2.75 (s, 2H), 2.60 (t, 2H, J=6.5 Hz), 2.42–2.38 (m, 4H), 1.70–1.58 (m, 4H), 1.58–1.35 (m, 2H).

EXAMPLE NO. 12

(Compound No. 20 in Scheme 4)

11-[4-(2-Azepan-1-yl-ethoxy)-benzyl]-8-benzyloxy-3-methoxy-5,11-dihydro-6H-benzo[a]carbazole

20 was prepared analogously to #19 except that the amine used was hexamethyleneimine. The product was isolated as an oil: $^1$H NMR (DMSO) 7.52–7.12 (m, 8H), 6.98–6.82 (m, 5H), 6.80 (dd, 1H, J=8.4 Hz, 2.6 Hz), 6.73 (dd, 1H, J=8.8 Hz, 2.4 Hz), 5.56 (s, 2H), 5.10 (s, 2H), 3.97 (t, 2H, J=6.0 Hz), 3.73 (s, 3H), 2.85–2.70 (m, 6H), 2.68–2.62 (m, 4H), 1.70–1.43 (m, 8 H).

EXAMPLE NO. 13

(Compound No. 21 in Scheme 4)

3-Methoxy-11-[4-(2-piperidin-1-yl-ethoxy)-benzyl]-5,11-dihydro-6H-benzo[a]carbazol-8-ol Compound #19 (3.2 g) was dissolved in THF/EtOH (30 mL, 1:1) and treated with 10% Pd/C (1.2 g) and cyclohexadiene (8 mL). The reaction was stirred at room temperature for 3 h and then filtered through celite and concentrated. The crude product was precipitated from methanol to yield #21 (1.3 g) as a white solid: Mp=141–143° C., $^1$H NMR (DMSO) 8.75 (s, 1H), 7.27 (d, 1H, J=8.5 Hz), 7.09 (d, 1H, J=8.5 Hz), 7.00–6.90 (m, 3H), 6.84 (d, 2H, J=8.8 Hz), 6.80 (d, 1H, J=2.4 Hz), 6.70 (dd, 1H, J=8.4 Hz, 2.6 Hz), 6.58 (dd, 1H, 8.8 Hz, 2.4 Hz), 5.45 (s, 2H), 3.98 (t, 2H, J=6.0 Hz), 3.70 (s, 3H), 2.89 (t, 2H, J=6.6 Hz), 2.75 (t, 2H, J=6.5 Hz), 2.60 (t, 2H, J=6.5 Hz), 2.40–2.30 (m, 4H), 1.53–1.40 (m, 4H), 1.39–1.30 (m, 2H); MS [M+H] observed at m/z=483; CHN calcd for C$_{31}$H$_{34}$N$_2$O$_3$+0.60 H$_2$O.

EXAMPLE NO. 14

(Compound No. 22 in Scheme 4)

11-[4-(2-Azepan-1-yl-ethoxy)-benzyl]-3-methoxy-5,11-dihydro-6H-benzo[a]carbazol-8-ol Reaction was performed analogously to that described for the synthesis of example #21: Mp=115–118° C.; $^1$H NMR (DMSO) 8.74 (s, 1H), 7.27 (d, 1H, J=8.5 Hz), 7.08 (d, 1H, J=8.5 Hz), 7.0–6.90 (m, 3H), 6.84 (d, 2H, J=8.8 Hz), 6.80 (d, 1H, J=2.4 Hz), 6.71 (dd, 1H, J=8.5 Hz, 2.6 Hz), 6.58 (dd, 1H, J=8.8 Hz, 2.4 Hz), 5.48 (s, 2H), 3.94 (t, 2H, J=6.0 Hz), 3.72 (s, 3H), 2.87 (t, 2H, J=6.6 Hz), 2.80–2.73 (m, 4H), 2.64–2.60 (m, 4H, J=4.4 Hz), 1.60–1.45 (m, 8H); IR (KBr) 3400, 2900, 1500, 1250; MS (−) FAB m/z 495 (M−H)$^-$; CHN calcd for C$_{32}$H$_{36}$N$_2$O$_3$+.33 CH$_3$OH.

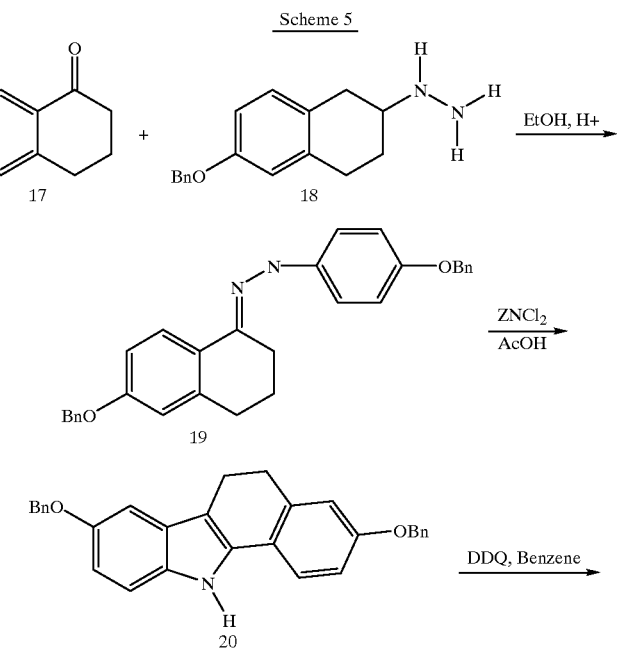

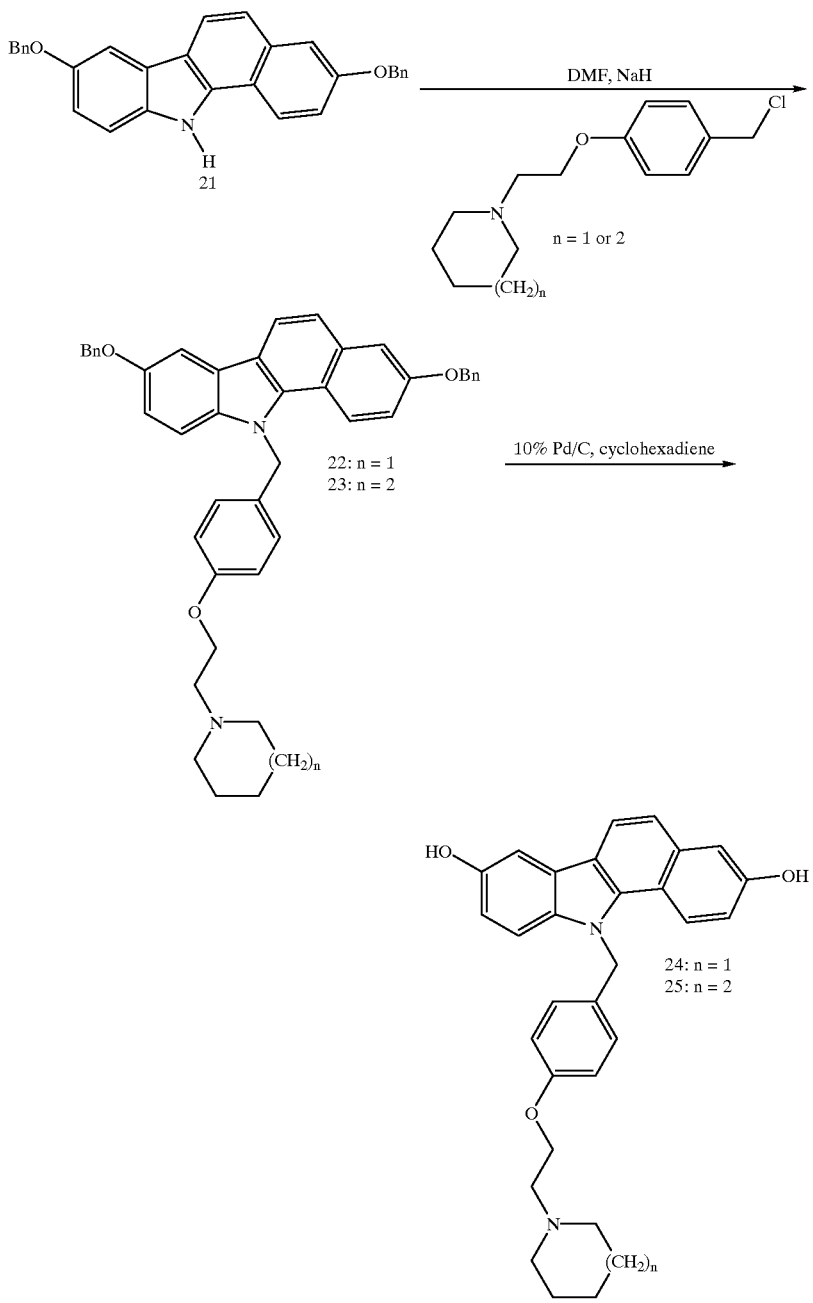

The benzocarbazoles of Scheme 5 were prepared analogously to the dihydro compounds, however, the added step of oxidizing the dihydrocarbazole intermediate 20 using 2,3-Dichloro-5,6-dicyanobenzoquinone (DDQ) was inserted into the sequence.

EXAMPLE NO. 15

(Hydrazone 19 in Scheme 5)

A solution consisting of 4-benzyloxyphenylhydrazide 18 (8 g, 37.3 mmol), 4-bezyloxytetralone 17 (11.3 g, 44.8 mmol), AcOH (5 drops) in EtOH (100 mL) was heated to reflux for 3 hours during which time all of the reactants went into solution. The reaction was cooled to 0° C. and the product precipitated out and was filtered out. The product 20 (9.5 g) was isolated as a white solid: mp 102–104° C. We found that the product was best used immediately because the products sitting out at room temperature results in discoloration.

EXAMPLE NO. 16

(Dihydrobenzocarbazole 20 in Scheme 5)

3,8-Bis-benzyloxy-5,11-dihydro-6H-benzo[a]carbazole

The hydrazone 19 (7.5 g, 16.7 mmol) was dissolved in AcOH (50 mL) and treated with $ZnCl_2$ (5.7 g, 42 mmol) and then heated at 105° C. for 15 minutes during which time everything went into solution. The reaction was allowed to room temperature and worked up by partitioning the reaction mixture between Et$_2$O and H$_2$O. The product 20, which was soluble in neither layer was isolated by filtering the biphasic mixture. The product was isolated as a white solid (5.6 g): mp 177–180° C.; MS APCI 430 (M–H).

EXAMPLE NO. 17

(Benzocarbazole 5 in Scheme 5)

3,8-Bis-benzyloxy-11H-benzo[a]carbazole

The dihydrocarbazole 20 (5.1 g, 11.9 mmol) in benzene (50 mL) was treated with DDQ (3.2 g, 14 mmol) and heated at reflux for 3 hours. The crude reaction mixture was partitioned between EtOAc and H$_2$O and the product, which was soluble in neither layer, was filtered off. The crude precipitate thus filtered was triturated with Et$_2$O to yield the desired material 21 as a light grey solid (3.4 g): mp 244–248° C.; MS eI 429.

EXAMPLE NO. 18

(Alkylated Benzocarbazole 22 in Scheme 5)

3,8-Bis-benzyloxy-11-[4-(2-piperdin-1-yl-ethoxy)-benzyl]-11H-benzo[a]carbazole

The benzocarbazole 21 (1.2 g, 2.8 mmol) was put in DMF (30 mL) (starting material appears insoluble in this solvent) and cooled to 0° C. and treated with NaH (60% dispersion in mineral oil, 300 mg, 7.8 mmol) and stirred at 0° C. for 15 minutes. The piperidinoethoxy benzyl chloride side chain was added (0.97 g, 3.3 mmol) and the reaction stirred an additional 15 minutes at 0° C. followed by 1 h at rt. The reaction was partitioned between EtOAc and H$_2$O and the product, which was soluble in neither layer, was filtered off. The product was triturated with Et$_2$O to yield the desired product 6 (1.3 g) as a white solid: mp=171–173° C.; MS (+) ESI 647 (M+H).

EXAMPLE NO. 19

(Alkylated Benzocarbazole 23 in Scheme 5)

11-[4-(2-Azepan-1-yl-ethoxy)-benzyl]-3,8-bis-benzyloxy-11H-benzo[a]carbazole

Benzocarbazole 23 was prepared analogously to benzocarbazole 22: mp 175–177° C.; MS ESI (+) 661 (M+H).

EXAMPLE NO. 20

(Benzocarbazole 24 in Scheme 5)

11-[4-(2-Piperidin-1-yl-ethoxy)-benzyl]-11H-benzo[a]carbazole-3,8-diol

A solution consisting of protected benzocarbazole 22 (1.15 g) in THF/EtOH (75:25) was treated with cyclohexadiene (4.5 mL) and 10% Pd/C (0.45 g) and allowed to stir at room temperature overnight. The solution was filtered through Celite and chromatographed on silica gel (10% MeOH/CH$_2$Cl$_2$) to yield the product which was triturated with Et$_2$O to render the product as a light grey solid: mp 249–251° C.; $^1$H NMR (DMSO) δ 9.68 (s, 1H), 9.05 (s, 1H), 8.21 (d, 1H, J=9.2 Hz), 8.04 (d, 1H, J=8.5 Hz), 7.48 (d, 1H, J=2.2 Hz), 7.46–7.40 (m, 2H), 7.26 (d, 1H, J=2.4 Hz), 6.70–6.96 (m, 3H), 6.89 (dd, 1H, J=8.7 Hz, 2.2 Hz), 6.83 (d, 2H, J=8.6 Hz), 5.92 (s, 2H), 3.95 (t, 2H, J=5.8 Hz), 2.63–2.55 (m, 2H), 2.42–2.33 (m, 4H), 1.50–1.42 (m, 4H), 1.38–1.29 (m, 2H); MS ESI (+) 467 (M+H).

EXAMPLE NO. 21

(Benzocarbazole 25 in Scheme 5)

11-[4-(2-Azepan-1-yl-ethoxy)-benzyl]-11H-benzo[a]carbazole 3,8-diol

Benzocarbazole 25 was prepared analogously to benzocarbazole 23: mp 204–206° C.; $^1$H NMR (DMSO) δ 9.7 (br s, 1H), 9.1 (br s, 1H), 8.21 (d, 1H, J=9.2 Hz), 8.04 (d, 1H, J=8.5 Hz), 7.48 (d, 1H, J=2.2 Hz), 7.46–7.40 (m, 2H), 7.26 (d, 1H, J=2.39 Hz), 7.02–6.97 (m, 3H), 6.88 (dd, 1H, J=8.7 Hz, 2.1 Hz), 6.82 (d, 2H, J=8.6 Hz), 5.92 (s, 2H), 3.92 (t, 2H, J=6.0 Hz), 2.76 (t, 2H, J=6.0 Hz), 2.65–2.57 (m, 4H), 1.57–1.48 (m, 8H); MS ESI (+) 481 (M+H).

Biological Data
In vitro Estrogen Receptor Binding Assay
Receptor Preparation

CHO cells overexpressing the estrogen receptor were grown in 150 mm$^2$ dishes in DMEM+10% dextran coated charcoal, stripped fetal bovine serum. The plates were washed twice with PBS and once with 10 mM Tris-HCl, pH 7.4, 1 mM EDTA. Cells were harvested by scraping the surface and then the cell suspension was placed on ice. Cells were disrupted with a hand-held motorized tissue grinder using two, 10-second bursts. The crude preparation was centrifuged at 12,000 g for 20 minutes followed by a 60 minute spin at 100,000 g to produce a ribosome free cytosol. The cytosol was then frozen and stored at –80° C. Protein concentration of the cytosol was estimated using the BCA assay with reference standard protein.

Binding Assay Conditions

The competition assay was performed in a 96-well plate (polystyrene*) which binds <2.0% of the total input [$^3$H]-17β-estradiol and each data point was gathered in triplicate. 100uG/100 uL of the receptor preparation was aliquoted per well. A saturating dose of 2.5 nM [$^3$H]17β-estradiol+ competitor (or buffer) in a 50 uL volume was added in the preliminary competition when 100× and 500× competitor were evaluated, only 0.8 nM [$^3$H] 17β-estradiol was used. The plate was incubated at room temperature for 2.5 h. At the end of this incubation period 150 uL of ice-cold dextran coated charcoal (5% activated charcoal coated with 0.05% 69K dextran) was added to each well and the plate was immediately centrifuged at 99 g for 5 minutes at 4° C. 200 uL of the supernatant solution was then removed for scintillation counting. Samples were counted to 2% or 10 minutes, whichever occurs first. Because polystyrene absorbs a small amount of [$^3$H] 17βestradiol, wells containing radioactivity and cytosol, but not processed with charcoal were included to quantitate amounts of available isotope. Also, wells containing radioactivity but no cytosol were processed with charcoal to estimate unremovable DPM of [$^3$H] 17β-estradiol.

Analysis of Results

Counts per minute (CPM) of radioactivity were automatically converted to disintegrated per minute (DPM) by the Beckman LS 7500 Scintillation Counter using a set of quenched standards to generate a H# for each sample. To calculate the % of estradiol binding in the presence of 100 or fold 500 fold competitor the following formula was applied:

((DPM sample-DPM not removed by charcoal/(DPM estradiol-DPM not removed by charcoal))×100%=% of estradiol binding For the generation of IC$_{50}$ curves, % binding is plotted vs compound. IC$_{50}$'s are generated for compounds that show >30% competition at 500× competitor concentration.

TABLE 2

Estrogen Receptor Binding

X = (CH$_2$)$n$

| Compound # | n | Z | Receptor Binding IC50's uM |
|---|---|---|---|
| Cmpd. 6 (Scheme 2) | 1 |  | 0.43 |
| Cmpd. 21 (Scheme 4) | 2 |  | 0.11 |
| Cmpd. 22 (Scheme 4) | 2 |  | 0.19 |

2× VIT ERE Infection Assay

Cell Maintenance and Treatment

Chinese Hamster Ovary cell (CHO) which had been stably transfected with the human estrogen receptor were maintained in DMEM+10% fetal bovine serum (FBS). 48 h prior to treatment the growth medium was replaced with DMEM lacking phenol red+10% dextran coated charcoal stripped FBS (treatment medium). Cells were plated at a density of 5000 cells/well in 96-well plates containing 200 µl of medium/well.

Calcium Phosphate Transfection

Reporter DNA (Promega plasmid pGL2 containing two tandem copies of the vitellogenin ERE in front of the minimal thymidine kinase promoter driving the luciferase gene) was combined with the B-galactosidase expression plasmid pCH110 (Pharmacia) and carrier DNA (pTZ18U) in the following ratio:

10uG of reporter DNA
5uG of pCH110DNA
5 uG of pTZ18U
20 uG of DNA/1 mL of transfection solution The DNA (20 uG) was dissolved in 500 uL of 250 mM sterile CaCl$_2$ and added dropwise to 500 uL of 2×HeBS (0.28 M NaCl, 50 mM HEPES, 1.5 mM Na$_2$HPO$_4$, pH 7.05) and incubated at room temperature for 20 minutes. 20 uL of this mixture was added to each well of cells and remained on the cells for 16 h. At the end of this incubation the precipitate was removed, the cells were washed with media, fresh treatment media was replaced and the cells were treated with either vehicle, 1 nM 17β-estradiol, 1 uM compound or 1 uM compound+1 nM 17β-estradiol (tests for estrogen antagonism). Each treatment condition was performed on 8 wells (n=8) which were incubated for 24 h prior to the luciferase assay.

Luciferase Assay

After 24 h exposure to compounds, the media was removed and each well washed 2× with 125 uL of PBS lacking Mg$^{++}$ and Ca$^{++}$. After removing the PBS, 25 uL of Promega lysis buffer was added to each well and allowed to stand at room temperature for 15 min, followed by 15 min at −80° C. and 15 min at 37° C. 20 uL, of lysate was transferred to an opaque 96 well plate for luciferase activity evaluation and the remaining lysate (5 uL) was used for the B-galactosidase activity evaluation.

(normalize transfection). The luciferan substrate (Promega) was added in 100 uL aliquots to each well automatically by the luminometer and the light produced (relative light units) was read 10 seconds after addition.

Infection Luciferase Assay (Standards)

| Compound | % Activation |
|---|---|
| 17β-estradiol | 100% activity |
| estriol | 38% activity |
| Raloxifene | 0% |

B-Galactosidase Assay

To the remaining 5 uL of lysate 45 uL of PBS was added. Then 50 uL of Promega B-galactosidase 2× assay buffer was added, mixed well and incubated at 37° C. for 1 hour. A plate containing a standard curve (0.1 to 1.5 milliunits in triplicate) was set up for each experimental run. The plates were analyzed on a Molecular Devices spectrophotometric plate reader at 410 nm. The optical densities for the unknown were converted to milliunits of activity by mathematical extrapolation from the standard curve.

Analysis of Results

The luciferase data was generated as relative light units (RLUs) accumulated during a 10 second measurement and automatically transferred to a JMP (SAS Inc) file where background RLUs were subtracted. The B-galactosidase values were automatically imported into the file and these values were divided into the RLUs to normalize the data. The mean and standard deviations were determined from a n=8 for each treatment. Compounds activity was compared to 17β-estradiol for each plate. Percentage of activity as compared to 17β-estradiol was calculated using the formula %=((Estradiol-control)/(compound value))×100.

TABLE 3

Infection Luciferase Activity

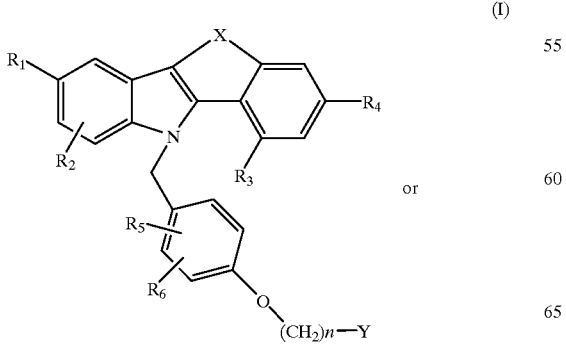

X = (CH₂)n

| Compound # | n | Z | 1 uM | 1 uM + 17β estradiol |
|---|---|---|---|---|
| Cmpd. 6 (Scheme 2) | 1 | piperidine | −2 | 83 |
| Cmpd. 21 (Scheme 4) | 2 | piperidine | −7 | 1 |
| Cmpd. 22 (Scheme 4) | 2 | piperidine | 1 | 8 |

As can be seen from the data in Table 2, the benzo[a] carbazoles (#21 and #22) bind better to the ER receptor than the indenoindole #6. From the infection luciferase assay data in Table 3, it can be seen that none of the compounds show significant agonistic activity on this promoter. Benzo[a] carbazoles show an ability to antagonize the effects of estradiol to baseline or almost baseline levels.

What is claimed:

1. A pharmaceutical composition comprising one or more estrogens and a compound having the structure:

(I)

[structure of compound I with R₁, R₂, R₃, R₄, R₅, R₆, X, and (CH₂)n—Y substituents]

or

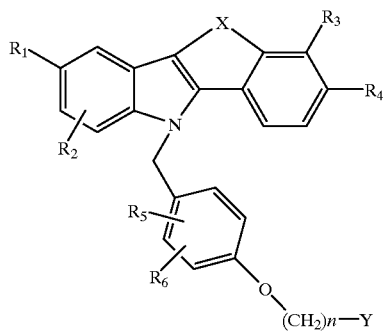

(II)

wherein:
R₁ is selected from H, OH or the C₁–C₄ esters or alkyl ethers thereof, or halogen;
R₂, R₃, R₄, R₅, and R₆ are independently selected from H, OH or the C₁–C₄ esters or alkyl ethers thereof, halogen, cyano, C₁–C₆ alkyl, or trifluoromethyl, with the proviso that, when R₁ is H, R₂ is not OH;
X is —CH=CH— or (CH₂)$_{n'}$
n' is 1 or 2
n is 2–4;
Y is selected from:
a) the moiety:

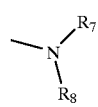

wherein R₇ and R₈ are independently selected from the group of H, C₁–C₆ alkyl, phenyl;

b) a five-membered saturated, unsaturated or partially unsaturated heterocycle containing up to two heteroatoms selected from the group consisting of —O—, —NH—, —N(C₁C₄ alkyl)—, —N=, and —S(O)$_m$—, wherein m is an integer of from 0–2, optionally substituted with 1–3 substituents independently selected from the group consisting of hydrogen, hydroxyl, halo, C₁–C₄ alkyl, trihalomethyl, C₁–C₄ alkoxy, trihalomethoxy, C₁–C₄ acyloxy, C₁–C₄ alkylthio, C₁–C₄ alkylsulfinyl, C₁–C₄ alkylsulfonyl, hydroxy (C₁–C₄)alkyl, phenyl optionally substituted with 1–3 (C₁–C₄)alkyl, —CO₂H—, —CN—, —CONHR¹—, —NH₂—, C₁–C₄ alkylamino, C₁–C₄ dialkylamino, —NHSO₂R¹—, —NHCOR¹—, —NO₂—;

c) a six-membered saturated, unsaturated or partially unsaturated heterocycle containing up to two heteroatoms selected from the group consisting of —O—, —NH—, —N(C₁C₄ alkyl)—, —N=, and —S(O)$_m$—, wherein m is an integer of from 0–2, optionally substituted with 1–3 substituents independently selected from the group consisting of hydrogen, hydroxyl, halo, C₁–C₄ alkyl, trihalomethyl, C₁–C₄ alkoxy, trihalomethoxy, C₁–C₄ acyloxy, C₁–C₄ alkylthio, C₁–C₄ alkylsulfinyl, C₁–C₄ alkylsulfonyl, hydroxy (C₁–C₄)alkyl, phenyl optionally substituted with 1–3 (C₁–C₄)alkyl, —CO₂H—, —CN—, —CONHR¹—, —NH₂—, C₁–C₄ alkylamino, C₁–C₄ dialkylamino, —NHSO₂R¹—, —NHCOR¹—, —NO₂—;

d) a seven-membered saturated, unsaturated or partially unsaturated heterocycle containing up to two heteroatoms selected from the group consisting of —O—, —NH—, —N($C_1C_4$ alkyl)—, —N=, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, phenyl substituted with 1–3 ($C_1$–$C_4$)alkyl, —$CO_2H$—, —CN—, —$CONHR^1$—, —$NH_2$—, $C_1$–$C_4$ alkylamino, $C_1$–$C_4$ dialkylamino, —$NHSO_2R^1$—, —$NHCOR^1$—, —$NO_2$—; or
e) a bicyclic ring system consisting of a five or six-membered heterocyclic ring fused to a phenyl ring, said heterocyclic ring containing up to two heteroatoms selected from the group of —O—, —NH—, —N($C_1C_4$ alkyl)—, and —S(O)$_m$—, wherein m is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, phenyl substituted with 1–3 ($C_1$–$C_4$)alkyl, —$CO_2H$—, —CN—, —$CONHR^1$—, —$NH_2$—, $C_1$–$C_4$ alkylamino, $C_1$–$C_4$ dialkylamino, —$NHSO_2R^1$—, —$NHCOR^1$—, —$NO_2$—;
or a pharmaceutically acceptable salt thereof.

2. A pharmaceutical composition of claim 1 wherein:
X is $(CH_2)_{n'}$
n' is 1
$R_1$ is selected from H, OH or the $C_1$–$C_4$ esters or alkyl ethers thereof, halogen;
$R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;
Y is the moiety

$R_7$ and $R_8$ are selected independently from H, $C_1$–$C_6$ alkyl, or combined by —(CH$_2$)p—, wherein p is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$), —$NH_3$, $C_1$–$C_4$ alkylamino, $C_1$–$C_4$ dialkylamino, —$NHSO_2$($C_1$–$C_4$), —NHCO ($C_1$–$C_4$), and —$NO_3$;
or a pharmaceutically acceptable salt thereof.

3. A pharmaceutical composition of claim 2 wherein the one or more estrogens are conjugated estrogenic hormones.

4. A pharmaceutical composition of claim 1 wherein:
X is $(CH_2)_{n'}$
n' is 2
$R_1$ is selected from H, OH or the $C_1$–$C_4$ esters or alkyl ethers thereof, halogen;
$R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;
Y is the moiety

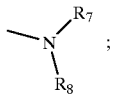

$R_7$ and $R_8$ are selected independently from H, $C_1$–$C_6$ alkyl, or combined by —(CH$_2$)p—, wherein p is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$), —$NH_3$, $C_1$–$C_4$ alkylamino, $C_1$–$C_4$ dialkylamino, —$NHSO_2$($C_1$–$C_4$), —NHCO ($C_1$–$C_4$), and —$NO_3$;
or a pharmaceutically acceptable salt thereof.

5. A pharmaceutical composition of claim 4 wherein the one or more estrogens are conjugated estrogenic hormones.

6. A pharmaceutical composition of claim 1 wherein:
X is $(CH_2)_{n'}$
n' is 1
$R_1$ is OH;
$R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;
X is selected from the group of Cl, $NO_2$, CN, $CF_3$, or $CH_3$;
Y is the moiety

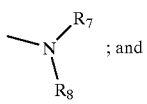

$R_7$ and $R_8$ are concatenated together as —(CH$_2$)$_r$—, wherein r is an integer of from 4 to 6, to form a ring optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH($C_1$–$C_4$), —$NH_3$, $C_1$–$C_4$ alkylamino, $C_1$–$C_4$ dialkylamino, —$NHSO_2$($C_1$–$C_4$), —NHCO ($C_1$–$C_4$), and —$NO_3$;
or a pharmaceutically acceptable salt thereof.

7. A pharmaceutical composition of claim 6 wherein the one or more estrogens are conjugated estrogenic hormones.

8. A pharmaceutical composition of claim 1 wherein:
X is $(CH_2)_{n'}$
n' is 2
$R_1$ is OH;
$R_2$, $R_3$, $R_4$, $R_5$, and $R_6$ are independently selected from H, OH or the $C_1$–$C_4$ esters or alkyl ethers thereof, halogen, cyano, $C_1$–$C_6$ alkyl, or trifluoromethyl, with the proviso that, when $R_1$ is H, $R_2$ is not OH;
X is selected from the group of Cl, $NO_2$, CN, $CF_3$, or $CH_3$;

Y is the moiety

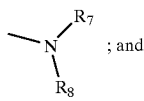
; and

R$_7$ and R$_8$ are concatenated together as —(CH$_2$)$_r$—, wherein r is an integer of from 4 to 6, to form a ring optionally substituted by up to three substituents selected from the group of hydrogen, hydroxyl, halo, C$_1$–C$_4$ alkyl, trihalomethyl, C$_1$–C$_4$ alkoxy, trihalomethoxy, C$_1$–C$_4$ alkylthio, C$_1$–C$_4$ alkylsulfinyl, C$_1$–C$_4$ alkylsulfonyl, hydroxy (C$_1$–C$_4$)alkyl, —CO$_2$H, —CN, —CONH(C$_1$–C$_4$), —NH$_2$, C$_1$–C$_4$ alkylamino, C$_1$–C$_4$ dialkylamino, —NHSO$_2$(C$_1$–C$_4$), —NHCO (C$_1$–C$_4$), and —NO$_2$;

or a pharmaceutically acceptable salt thereof.

9. A pharmaceutical composition of claim 8 wherein the one or more estrogens are conjugated estrogenic hormones.

10. A pharmaceutical composition of claim 1 comprising one or more estrogens and 8-Benzyl-2-methoxy-5-[4-(2-piperidin-1-yl-ethoxy)-benzyl]-5,10-dihydro-indeno[1,2-b]indole.

11. A pharmaceutical composition of claim 1 comprising one or more estrogens and 2-Methoxy-5-[4-(2-piperidin-1-yl-ethoxy)-benzyl]-5,10-dihydro-indeno[1,2-b]indol-8ol.

12. A pharmaceutical composition of claim 1 comprising one or more estrogens and 11-[4-(2-Azepan-1-yl-ethoxy)-benzyl]-8-benzyloxy-3-methoxy-5,11-dihydro-6H-benzo[a]carbazole.

13. A pharmaceutical composition of claim 1 comprising one or more estrogens and 11-[4-(2-Azepan-1-yl-ethoxy)-benzyl]-3-methoxy-5,11-dihydro-6H-benzo[a]carbazol-8-ol.

14. A pharmaceutical composition of claim 1 comprising one or more estrogens and 3-Methoxy-8-benzyloxy-11-[4-(2-piperidin-1-yl-ethoxy)-benzyl]-5,11-dihydro-6H-benzo[a]carbazole.

15. A pharmaceutical composition of claim 1 comprising one or more estrogens and 3-Methoxy-11-[4-(2-piperidin-1-yl-ethoxy)-benzyl]-5,11-dihydro-6H-benzo[a]carbazol-8-ol.

16. A pharmaceutical composition of claim 1 wherein the one or more estrogens are selected from equilin, equilenin, ethinyl estradiol, 17β-estradiol, dihydroequilenin, 17β-dihydroequilenin, menstranol, conjugated estrogens, sulfate esters of estrone, Sodium estrone sulfate, Sodium equilin sulfate, Sodium 17alpha-dihydroequilin sulfate, Sodium 17alpha-estradiol sulfate, Sodium Delta8,9 -dehydroestrone sulfate, Sodium equilenin sulfate, Sodium 17beta-dihydroequilin sulfate, Sodium 17alpha-dihydroequilenin sulfate, Sodium 17beta-estradiol sulfate, Sodium 17beta-dihydroequilenin sulfate, Estrone 3-sodium sulfate, Equilin 3-sodium sulfate, 17alpha-Dihydroequilin 3-sodium sulfate, 3beta-Hydroxy-estra-5(10), 7-dien-17-one 3-sodium sulfate, 5alpha-Pregnan-3beta-20R-diol 20-sodium sulfate, 5alpha-Pregnan-3beta, 16alpha-diol,20-one 3-sodium sulfate, delta (8,9)-Dehydroestrone 3-sodium sulfate, Estra-3beta, 17alpha-diol 3-sodium sulfate, 3beta-Hydroxy-estr-5(10)-en, 17-one 3-sodium sulfate or 5alpha-Pregnan-3beta, 16alpha, 20R-triol 3-sodium sulfate, equol or enterolactone; or a pharmaceutically acceptable salt or ester thereof.

17. A pharmaceutical composition comprising one or more estrogens and a compound having the structure:

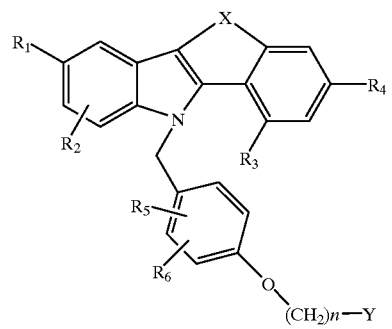

or

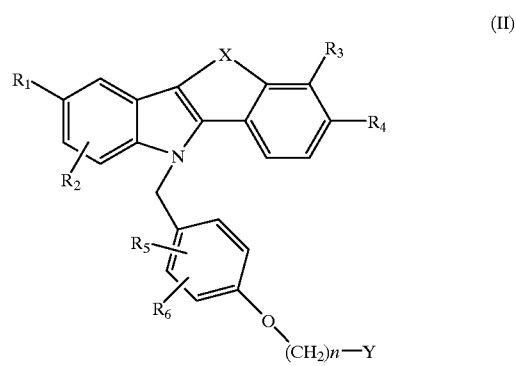

wherein:
R$_1$ is selected from H, OH or the C$_1$–C$_4$ esters or alkyl ethers thereof, or halogen;
R$_2$, R$_3$, R$_4$, R$_5$, and R$_6$ are independently selected from H, OH or the C$_1$–C$_4$ esters or alkyl ethers thereof, halogen, cyano, C$_1$–C$_6$ alkyl, or trifluoromethyl, with the proviso that, when R$_1$ is H, R$_2$ is not OH;
X is —CH=CH— or (CH$_2$)$_{n'}$
n' is 1 or 2
n is 2–4;
Y is selected from:
a) the moiety:

wherein R$_7$ and R$_8$ are independently selected from the group of H, C$_1$–C$_6$ alkyl, phenyl;
b) the moiety:

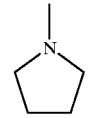

optionally substituted with 1–3 substituents independently selected from the group consisting of hydrogen, hydroxyl, halo, C$_1$–C$_4$ alkyl, trihalomethyl, C$_1$–C$_4$ alkoxy, trihalomethoxy, C$_1$–C$_4$ acyloxy, C$_1$–C$_4$ alkylthio, C$_1$–C$_4$ alkylsulfinyl, C$_1$–C$_4$ alkylsulfonyl, hydroxy (C$_1$–C$_4$)alkyl, phenyl optionally substituted with 1–3 (C$_1$–C$_4$)alkyl, —CO$_2$H—, —CN—, —CONHR$^1$—, —NH$_2$—, C$_1$–C$_4$ alkylamino, C$_1$–C$_4$ dialkylamino, —NHSO$_2$R$^1$—, —NHCOR$^1$—, —NO$_2$—;

c) the moiety:

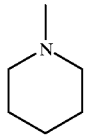

optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, phenyl optionally substituted with 1–3 ($C_1$–$C_4$)alkyl, —$CO_2H$—, —CN—, —$CONHR^1$—, —$NH_2$—, $C_1$–$C_4$ alkylamino, $C_1$–$C_4$ dialkylanino, —$NHSO_2R^1$—, —$NHCOR^1$—, —$NO_2$—; or d) the moiety:

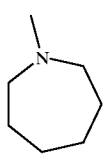

optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, phenyl substituted with 1–3 ($C_1$–$C_4$)alkyl, —$CO_2H$—, —CN—, —$CONHR^1$—, —$NH_2$—, $C_1$–$C_4$ alkylamino, $C_1$–$C_4$ dialkylamino, —$NHSO_2R^1$—, —$NHCOR^1$—, —$NO_2$—;

or a pharmaceutically acceptable salt thereof.

18. A pharmaceutical composition of claim 17 wherein the one or more estrogens are selected from equilin, equilenin, ethinyl estradiol, 17β-estradiol, dihydroequilenin, 17β-dihydroequilenin, menstranol, conjugated estrogens, sulfate esters of estrone, Sodium estrone sulfate, Sodium equilin sulfate, Sodium 17alpha-dihydroequilin sulfate, Sodium 17alpha-estradiol sulfate, Sodium Delta8,9-dehydroestrone sulfate, Sodium equilenin sulfate, Sodium 17beta-dihydroequilin sulfate, Sodium 17alpha-dihydroequilenin sulfate, Sodium 17beta-estradiol sulfate, Sodium 17beta-dihydroequilenin sulfate, Estrone 3-sodium sulfate, Equilin 3-sodium sulfate, 17alpha-Dihydroequilin 3-sodium sulfate, 3beta-Hydroxy-estra-5(10), 7-dien-17-one 3-sodium sulfate, 5alpha-Pregnan-3beta-20R-diol 20-sodium sulfate, 5alpha-Pregnan-3beta, 16alpha-diol,20-one 3-sodium sulfate, delta(8,9)-Dehydroestrone 3-sodium sulfate, Estra-3beta, 17alpha-diol 3-sodium sulfate, 3beta-Hydroxy-estr-5(10)-en, 17-one 3-sodium sulfate or 5alpha-Pregnan-3beta,16alpha, 20R-triol 3-sodium sulfate, equol or enterolactone; or a pharmaceutically acceptable salt or ester thereof.

19. A method of treating or preventing bone loss in a mammal, the method comprising administering to a mammal in need thereof an estrogen and an effective amount of a compound of claim 1, or a pharmaceutically acceptable salt thereof.

20. A method of treating or preventing disease states or syndromes which are caused or associated with an estrogen deficiency in a mammal, the method comprising administering to a mammal in need thereof an estrogen and an effective amount of a compound of claim 1, or a pharmaceutically acceptable salt thereof.

21. A method of treating or preventing cardiovascular disease in a mammal, the method comprising administering to a mammal in need thereof an estrogen and an effective amount of a compound of claim 1, or a pharmaceutically acceptable salt thereof.

* * * * *